United States Patent [19]
Horn

[11] Patent Number: 5,528,557
[45] Date of Patent: Jun. 18, 1996

[54] ACOUSTIC EMISSION SOURCE LOCATION BY REVERSE RAY TRACING

[75] Inventor: Michael Horn, South Setauket, N.Y.

[73] Assignee: Northrop Grumman Corporation, Los Angeles, Calif.

[21] Appl. No.: 512,249

[22] Filed: Aug. 7, 1995

[51] Int. Cl.$^6$ .............................. G01S 3/80; G01N 29/00
[52] U.S. Cl. ....................... 367/129; 367/118; 367/907; 364/550; 73/587
[58] Field of Search ...................... 367/118, 124, 367/127, 129, 907; 73/583, 587; 364/507, 508, 550

[56] References Cited

U.S. PATENT DOCUMENTS

| | | | |
|---|---|---|---|
| 3,985,024 | 10/1976 | Horak | 73/587 |
| 4,910,718 | 3/1990 | Horn | 367/124 |
| 5,417,113 | 5/1995 | Hartley | 73/587 |

*Primary Examiner*—Ian J. Lobo
*Attorney, Agent, or Firm*—Terry J. Anderson; Karl J. Hoch, Jr.

[57] ABSTRACT

A method of locating an acoustic emission source in a structure by reverse ray tracing. An azimuth acoustic emission sensor is utilized which has an array of individual elemental detectors which independently and sequentially respond to the passage of an acoustic stress wave. The response of each element of the array is electronically monitored, and individual responses to the acoustic stress wave are analyzed to determine the azimuth approach angle of the wave to the azimuth acoustic emission sensor. An accurate measurement of the true location of the acoustic emission signal source is then provided by reverse ray tracing by using a parallel processing arrangement having a plurality of parallel processing elements. The structure is modeled in the computer on a one to one basis, with each parallel processing element simulating and having structural data on one discrete area of the structure. The determined azimuth approach angle is an input to the parallel processing arrangement, such that a simulated wave propagation takes place in the computer model as if it were propagating in the structure, and the actual location of the acoustic emission source is determined by reverse ray tracing by taking into account the structure of the intervening path of the wave and the most probable perturbations of the wave therein. The present invention has particular applicability to aircraft structures, and the method is utilized to locate structural defects therein.

7 Claims, 2 Drawing Sheets

ACOUSTIC EMISSION SOURCE LOCATION BY REVERSE RAY TRACING

BACKGROUND OF THE INVENTION

1. Field of the Invention

The present invention relates generally to acoustic emission monitoring systems. More particularly, the subject invention pertains to an acoustic emission monitoring system for locating a source of acoustic waves in a structural member such as an aircraft to detect structural defects therein. Structural defects such as stress cracks emit acoustic and stress waves which propagate outwardly therefrom. By monitoring the structure for acoustic emissions, the existence and location of defects such as stress cracks can be determined.

In greater detail, the present invention relates to a method of acoustic emission source location by reverse ray tracing which allows the structure along the intervening path of a detected wave and the most probable perturbations of the detected wave to be taken into account. The total of all of the iterative changes taken by the wave are calculated, providing a very accurate measurement of the path and the true location of the acoustic emission signal source.

The present invention has particular applicability to the testing of the structural integrity of aircraft. When minor flaws develop in an aircraft structure, elastic acoustic and stress waves are generated by the flaws, and it is important to be able to locate the source of the acoustic emissions so that appropriate repairs can be made. The present invention offers that capability.

The problem of an aging aircraft fleet is a cause for concern for our society, which has the busiest commercial air traffic system in the world and also the largest military aircraft inventory. The assured airworthiness of these aircraft places a burden on all involved, from the industries that build and maintain them, through to the government regulatory agencies responsible for maintaining adequate oversight thereof. Moreover, because of economic and political factors, military and commercial carriers are retaining their equipment longer than usual, putting a further strain on aircraft which are reaching the waning hours of their useful service life.

Furthermore, the dynamics of service-induced loads on an aging aircraft are not always the same as those experienced by a young, robust aircraft of the same family of aircraft. Commonly, in aging aircraft one finds that the repair and modifications themselves shift the strain loads to new areas, sometimes to uninspected areas, only noticed as a result of their failure. A system is required to perform constant assessments on the structural integrity of aging aircraft and also to inspect details in the complex structures of modern aircraft.

Acoustic emission monitoring is useful for global detection and location of cracks, impacts, delaminations and other fatigue damage in large scale structures such as aircraft because of the remote sensing capability of an acoustic emission monitoring system, and its use of a contiguous structure as a propagating medium for damage induced stress waves.

2. Discussion of the Prior Art

Acoustic emission monitoring is frequently used in aircraft to detect structural defects such as stress cracks which emit acoustic and stress waves which propagate outwardly therefrom. By monitoring the acoustic emissions, the existence and location of defects such as stress cracks can be determined.

The technological field of acoustic emission monitoring has several problems which must be overcome before a useful result is obtained from its application. One major problem is determining the precise location of the source of the acoustic emission signals.

To locate an acoustic emission signal source, some prior art systems require four piezoelectric sensors placed a measured distance from each other and surrounding the expected source of signals. As a stress wave propagates across a structure, it passes by each of the monitoring sensors. As each sensor is hit, a clock circuit is triggered until all of the sensors in the array have detected the passing stress wave, and the arrival time for each sensor is known. To deduce the origin of a stress wave, the differences in the arrival times are calculated for each set of two sensors in the grouping. The differences in arrival time, or $\Delta t$, for each set of two sensors represent a set of points. A plot of these locations generates the characteristic curve of a hyperbola, along which are the innumerable points from which the signal may have emanated. So, using this approach, two sensors tell little of the specific origins of signals. At least a third sensor and an additional $\Delta t$ is required to locate the signal source by the corresponding overlapping hyperbolas.

In order for any group of sensors to be able to cover a large area of a structure and also use a practical number of sensors, the sensors are typically deployed as far apart as possible. But in the intervening space between the sensors, the stress waves can be modulated by the complex structure so that each sensor may detect a wave with modified waveform characteristics which can distort the arrival times. Since conventional acoustic sensors cannot discriminate direction, they are prone to detect and accept signals from simultaneous sources, and interpret them as the same stress wave hitting the other sensors in the group. These disparities multiply as the errors of each arrival time are added into the location equation.

SUMMARY OF THE INVENTION

Accordingly, it is a primary object of the present invention to provide acoustic emission source location by utilizing an azimuth acoustic emission sensor to detect the azimuth of the final approach of the acoustic and stress wave, and by utilizing reverse ray tracing to solve the complex problem of determining the actual location of the source of the acoustic emissions. As a stress crack grows, it emits acoustic and stress waves which propagate outwardly from the point of origin. An azimuth acoustic emission sensor detects the wave and calculates the azimuth of the final approach angle of the acoustic and stress wave. If the azimuth acoustic emission sensor detects a wave propagating through a complex structure, the calculated azimuth relates only to the final approach of the acoustic and stress wave as it transits the face of the transducer. The projected line of the determined azimuth may not be an accurate indication of the actual location of the source of the acoustic emissions if a complex path was taken by the wave through the structure before reaching the transducer.

A further object of the subject invention is the provision of acoustic emission source location by reverse ray tracing which allows the structure of the intervening path and the most probable perturbations of the wave to be taken into account. The total of all of the iterative changes taken by the wave are calculated, providing a very accurate measurement of the path and the true location of the acoustic emission signal source.

In accordance with the teachings herein, the present invention provides a method of locating an acoustic emission source in a structure by reverse ray tracing. An azimuth acoustic emission sensor is utilized which has an array of individual elemental detectors which independently and sequentially respond to the passage of an acoustic stress wave. The response of each element of the array is electronically monitored, and individual responses to the acoustic stress wave are analyzed to determine the azimuth approach angle of the wave to the azimuth acoustic emission sensor. An accurate measurement of the true location of the acoustic emission signal source is then provided by reverse ray tracing by using a parallel processing arrangement having a plurality of parallel processing elements. The structure is modeled in the computer on a one to one basis, with each parallel processing element simulating and having structural data on one discrete area of the structure. The determined azimuth approach angle is an input to the parallel processing arrangement, such that a simulated wave propagation takes place in the computer model as if it were propagating in the structure, and the actual location of the acoustic emission source is determined by reverse ray tracing by taking into account the structure of the intervening path of the wave and the most probable perturbations of the wave therein.

In greater detail, the present invention has particular applicability to aircraft structures, and the method is utilized to locate structural defects therein. Preferably, the response of each element of the array is measured with a resolution of at least 100 nsec, with a clock which is triggered at the moment that the first of the elements output signal reaches a peak, and the clock runs until another element produces a signal peak, and the time difference between the peak signals is utilized as a measurement of the azimuth approach angle of the wave. Preferably the detection element, which is opposite to the detection element first actuated, is deactuated to provide greater signal processing accuracy and reduce wasted processing time and error in responding to the passage of two or more coincidental but separate waves. More than one azimuth acoustic sensor can be utilized to determine the azimuth approach location in two or more dimensions.

BRIEF DESCRIPTION OF THE DRAWINGS

The foregoing objects and advantages of the present invention for acoustic emission source location by reverse ray tracing may be more readily understood by one skilled in the art with reference being had to the following detailed description of several preferred embodiments thereof, taken in conjunction with the accompanying drawings wherein like elements are designated by identical reference numerals throughout the several views, and in which.

DETAILED DESCRIPTION OF THE DRAWINGS

Figure 1:
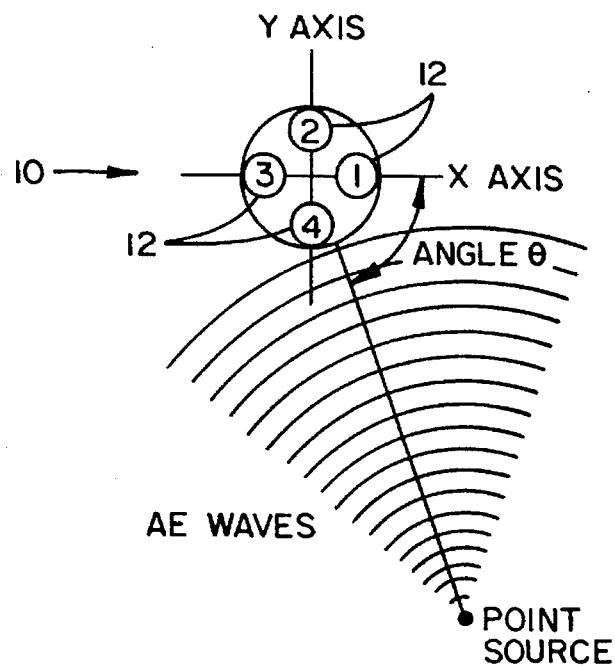
FIG. 1 illustrates an azimuth acoustic emission sensor which includes a plurality of individual elemental sensors combined in one sensor package.

Referring to the drawings in detail, FIG. 1 illustrates a new generation of azimuth acoustic emission sensor 10 which does not rely on the determination of arrival times of stress waves by widely separated sensors. The azimuth acoustic emission sensor 10 includes a plurality of individual elemental sensors 12 combined in one sensor package. The azimuth acoustic emission sensor 10 reduces the error of locating a signal source in a noisy work environment, and also reduces the number of sensors required to perform the task.

Figure 2:
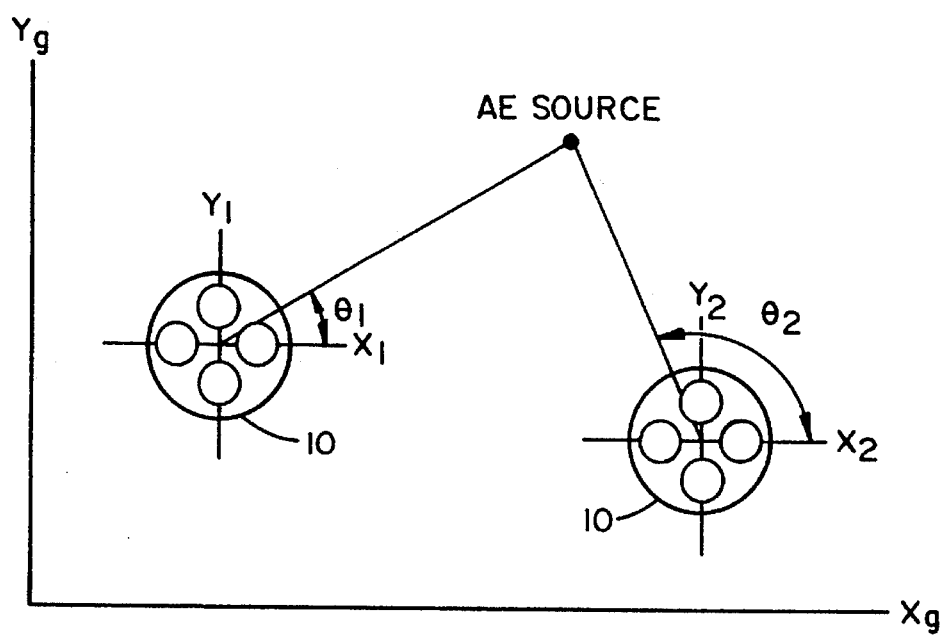
FIG. 2 illustrates two azimuth acoustic emission sensors as shown in FIG. 1, combined to accurately locate the source of a stress wave in two, and in some cases three, dimensions.

With this new approach, one individual azimuth acoustic emission sensor 10 provides sufficient data for its accompanying instrumentation to calculate an azimuth approach angle $\Theta$ from that sensor to the origin of the stress wave. As illustrated in FIG. 2, two such sensors 10 working together are capable of locating the source of the stress wave accurately in two, and in some cases three, dimensions by combining the calculated azimuth approach angles $\Theta_1$ and $\Theta_2$.

The azimuth acoustic emission sensor, as described in U.S. Pat. No. 4,910,718, combines several sensor elements in one package with an electronic circuit for analyzing the effects of an arriving stress wave on each element. The azimuth acoustic sensor, instrumentation and algorithms comprise the azimuth acoustic emission sensor system, and allow the signals of the azimuth acoustic sensor to be interpreted as a useful azimuth approach angle.

By isolating the plane of the sensor into individual elemental segments, the discrete elements of the sensor independently and sequentially respond to the passage of the acoustic and stress wave. Since the wave propagates only a fraction of an inch from one sensor element 12 to the next, no substantial modification of the wave occurs between elements 12.

Each element of the array is electronically monitored, and the individual responses to the acoustic and stress wave are analyzed with at least 100 nsec of resolution, which requires a clock speed in the order of 10 mHz. The clock is triggered at the moment that the first of the elements output signal reaches a peak. The clock runs until another element, likewise, produces a signal peak.

The time difference between the signal peaks can now be considered as a direct correlation to the angle of the translational displacement of the wave on a two dimensional plane. That is, for each $\Delta t$ generated between any two elements, a unique azimuth exists between the sensor and passing wave.

For example, $t_x = t_3 - t_1$, and $t_y = t_4 - t_2$, here $\Theta = \tan^{-1}(t_y/t_x)$.

Two dimensions are calculated simply by evaluating the intersection of two unique lines from the family of lines, $y = mx + b$.

Figure 3:
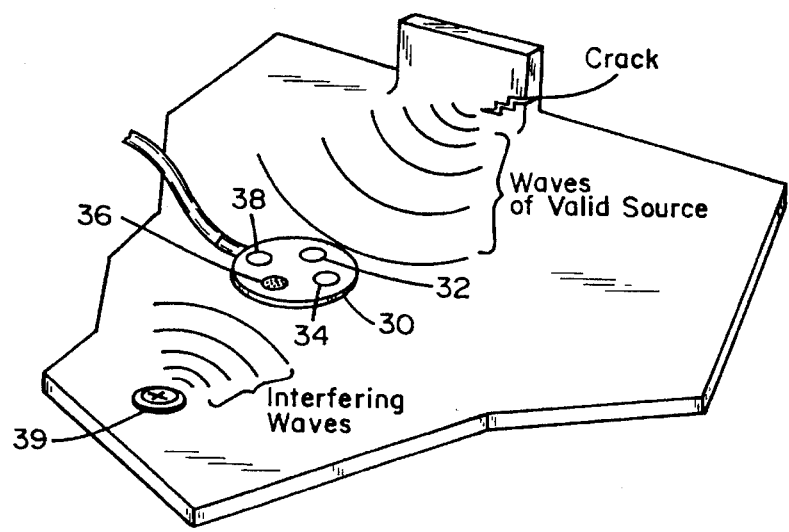
FIG. 3 illustrates a detection technique in which the detection element opposite to the detection element first actuated is deactuated to provide greater signal processing accuracy.

FIG. 3 illustrates a detection technique in which an azimuth acoustic emission sensor 30 has four individual detection elements 32, 34, 36 and 38, and the detection element 36 opposite to the detection element 32 first actuated is deactuated to provide greater signal processing accuracy. This reduces wasted time and error in responding to the passage of separate but coincidental waves, such as interfering waves emitted by a noisy fastener 39. This approach requires that the sensor consist of more than three elements, and can be structured such that, in the case of a six or more element array, the entire opposite half of the array would trigger such a deactivating response to prevent the inclusion of coincidental waves in the calculation of an azimuth approach angle. This technical approach is similar to the use of slave sensors in a conventional system, but without the necessity of deploying separate sensors and with the ability to adapt to changing conditions in real time.

The development of an azimuth calculating sensor as described in U.S. Pat. No. 4,910,718 enables the use of a new emerging technical approach used in ultrasonic inspection which is known as ray tracing. This technique, described in a number of treatises by Dr. Henry Chaskelis et al., discloses ways that the paths of ultrasonic waves to and from an ultrasonic transducer may be traced through complex structures. As used in acoustic emission detection, it would be an inverse application, or reverse ray tracing.

Figure 4:
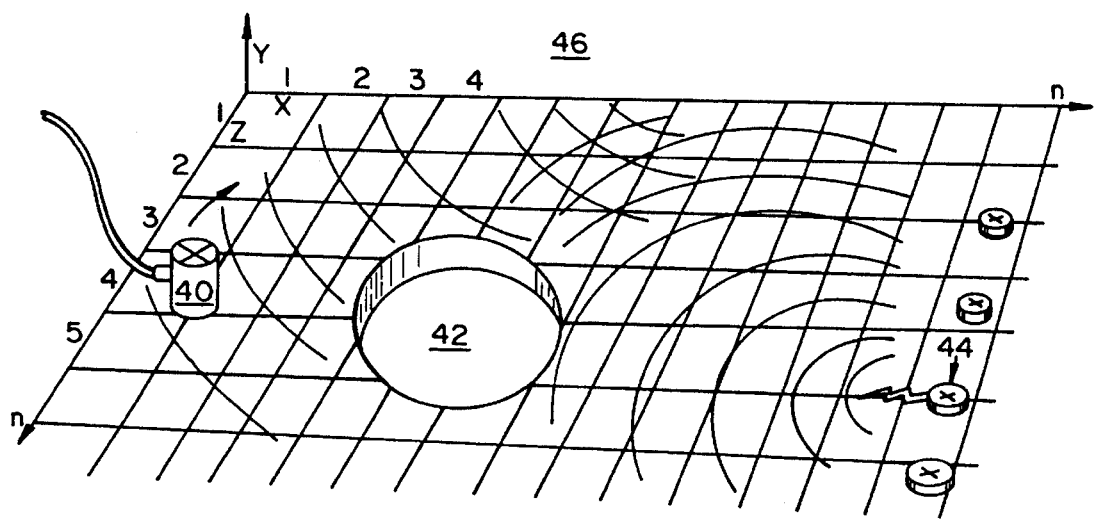
FIG. 4 is a perspective view of an exemplary application of acoustic emission source location by utilizing azimuth acoustic emission sensors combined with reverse ray tracing, deduced from the output of the azimuth acoustic sensor and a parallel processing computer arrangement, pursuant to the teachings of the present invention.

FIG. 4 is a perspective view of an exemplary application of acoustic emission source location by utilizing azimuth acoustic emission sensors to determine the final azimuth approach angle of the wave to the sensors, combined with reverse ray tracing. The approach uses a parallel processing arrangement which models the aircraft structure on a one to one basis, with each parallel processing element simulating and having structural data on a discrete area of the structure in a database. As illustrated in FIG. 4, the structure of one section of an aircraft, in which an acoustic azimuth emission detector 40 is located, can be divided in a computer model into a plurality of discrete areas, each of which has designated coordinates $X_{1-n}$, $Y_{1-n}$. The calculated azimuth approach angle is an input to the parallel processing arrangement and computer database, and pursuant to the teachings of the present invention, reverse ray tracing allows the structure of the intervening path and the most probable perturbations of the wave to be taken into account. The total of all of the iterative changes taken by the wave are calculated, providing a very accurate measurement of the path and the true location of the acoustic emission signal source.

The arrangements of FIGS. 1, 2 and 3 enable a precise determination of the azimuthal approach angle from which acoustic emissions are detected, but as illustrated in FIG. 4, that angle does not necessarily represent the direction towards the acoustic source, shown as a cracking structure. In the structure of FIG. 4, a handhole 42 is positioned between the azimuth acoustic emission sensor 40 and the acoustic source cracking structure 44, such that the strongest acoustic waves are reflected by a bulkhead structure 46 around the handhole 42 to the azimuth acoustic sensor 40.

The present invention utilizes reverse ray tracing to provide the true source location of the acoustic waves, which utilizes the output of the azimuth acoustic sensor, and a parallel processing arrangement which has a computer database on the structure around the azimuth acoustic sensor.

In the field of acoustic ray tracing, acoustic tomography is being developed by the Mechanics of Materials Branch at the Naval Research Laboratory. Acoustic tomography is much more difficult than x-ray tomography currently in medical use because of the bending of acoustic rays (refraction) and mode conversion at interfaces. In order to address acoustic tomography, the problem has been approached on two fronts: 1) the inversion of experimental data, and 2) a forward predictive wave propagation method. The predictive part or wave propagation simulator must work in an extremely fast and efficient manner for near real time application.

An approach, similar to finite difference calculations, has been developed for acoustic wave propagation in materials for computation on a massively parallel computer possibly having millions of real and virtual processors. This methodology uses the architecture of a massively parallel computer to model the materials/structures on a one to one correspondence, one processor for one material/structure element. In this way, the material/structure is modeled directly and easily by the massively parallel computer. With the incorporation of proper physics, wave propagation takes place in the computer model as if it were propagating in the material/structure. Any type of waveform can be used as an input to the computer, and a waveform can be experimentally measured and digitized and then used as an input for the computer.

In an aircraft, the material/structure has a fixed, known geometry and known material properties, which is placed in a computer database. Wave propagation simulation (forward wave propagation) is accomplished on the massively parallel computer as if it were the material. The complexity and size of the modeled material which is simulated is based upon a number of considerations including frequency, velocity range, the smallest physical detail, and the total size of the structure being modeled. These considerations are matched to the total number of processors of the massively parallel computer and the number of processors required per wavelength. The physical size of the structure is limited by the size of the parallel processing arrangement, or the structure could be divided into parts, and the propagation coupled from one part to another.

To locate the source of acoustic signals, both the displacement magnitudes and the propagation directions of the received signals are measured and digitized. The digitized signals are inputs to the massively parallel computer, and by using reciprocity the waves back propagate to locate and provide information about the actual location of the acoustic emission source. The possible information that can be determined about a source is whether it is omni-directional or directed, but this would require additional measurements. The amount of information that can be used is highly dependent on the information gathered by the receivers and how well the true physical material/structure is modeled in the massively parallel computer in terms of geometry and physical phenomena. If received signals are used for the forward simulation model, the propagating wave does not represent the true source of the signal, but instead represents the source as viewed by the receiver. The information gathered is colored by the receiver in terms of its frequency response, mode response (longitudinal, shear, etc.) and directionality. Even though an array receiver may give more meaningful directional information, the frequency and mode will still be colored by the receiver. In addition to coloring a signal with the response of the receivers, the massively parallel computer is currently limited to linear elastic wave propagation. Geometric attenuation and mode conversion are currently in the model, however, dispersion is not taken into account, nor is attenuation due to material absorption.

While several embodiments and variations of the present invention for acoustic emission source location by reverse ray tracing are described in detail herein, it should be apparent that the disclosure and teachings of the present invention will suggest many alternative designs to those skilled in the art.

What is claimed is:

1. A method of locating an acoustic emission source in a structure by reverse ray tracing comprising:

a. utilizing an azimuth acoustic emission sensor having an array of individual elemental detectors which independently and sequentially respond to the passage of an acoustic stress wave, electronically monitoring the response of each element of the array, and analyzing the individual responses to the acoustic stress wave to determine the azimuth approach angle of the wave to the azimuth acoustic emission sensor; and b. providing an accurate measurement of the true location of the acoustic emission signal source by reverse ray tracing by using a parallel processing arrangement having a plurality of parallel processing elements in which the structure is modeled in a computer on a one to one basis, with each parallel processing element simulating and having structural data on one discrete area of the structure in a database, and the determined azimuth approach angle is an input to the parallel processing arrangement, such that a simulated wave propagation takes place in the computer model as if it were propagating in the structure, and the actual location of the acoustic emission source is determined by reverse ray tracing by taking into account the structure of the intervening path and the most probable perturbations of the wave therein.

2. A method of locating an acoustic emission source in a structure by reverse ray tracing as claimed in claim 1, wherein the structure is an aircraft, and the method is utilized to locate structural defects therein.

3. A method of locating an acoustic emission source in a structure by reverse ray tracing as claimed in claim 1, wherein the response of each element of the array is measured with a resolution of at least 100 nsec, with a clock which is triggered at the moment that the first of the elements output signal reaches a peak, and the clock runs until another element produces a signal peak, and the time difference between the peak signals is utilized as a measurement of the azimuth approach angle of the wave.

4. A method of locating an acoustic emission source in a structure by reverse ray tracing as claimed in claim 1, wherein the displacement magnitudes and propagation directions of received signals are measured and digitized, and the digitized signals are inputs to the parallel processing arrangement.

5. A method of locating an acoustic emission source in a structure by reverse ray tracing as claimed in claim 1, wherein the complexity and size of the structure which is modeled in the computer is based upon considerations including frequency, velocity range, the smallest physical detail, and the total size of the structure being modeled, and the considerations are matched to the total number of processors of the parallel processing arrangement and the number of processors required per wavelength.

6. A method of locating an acoustic emission source in a structure by reverse ray tracing as claimed in claim 1, wherein the detection element which is opposite to the detection element first actuated is deactuated to provide greater signal processing accuracy, and reduce wasted processing time and error in responding to the passage of two or more coincidental but separate waves.

7. A method of locating an acoustic emission source in a structure by reverse ray tracing as claimed in claim 1, including utilizing more than one azimuth acoustic sensor to determine the azimuth approach location in two or more dimensions.

* * * * *